US010039940B2

(12) United States Patent
Terrisse

(10) Patent No.: US 10,039,940 B2
(45) Date of Patent: Aug. 7, 2018

(54) COMPOSITIONS AND METHODS FOR MINIMIZING AND/OR REDUCING THE APPEARANCE OF DEFECTS AROUND EYES

(75) Inventor: Isabelle Terrisse, Vitry sur Seine (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/288,724

(22) Filed: Nov. 3, 2011

(65) Prior Publication Data
US 2012/0053142 A1 Mar. 1, 2012

Related U.S. Application Data

(63) Continuation of application No. 12/437,055, filed on May 7, 2009, now abandoned.

(51) Int. Cl.
A61Q 19/00 (2006.01)
A61K 8/42 (2006.01)
A61K 8/49 (2006.01)
A61K 8/63 (2006.01)
A61K 8/73 (2006.01)

(52) U.S. Cl.
CPC .............. A61Q 19/005 (2013.01); A61K 8/42 (2013.01); A61K 8/494 (2013.01); A61K 8/63 (2013.01); A61K 8/735 (2013.01); A61K 2800/874 (2013.01)

(58) Field of Classification Search
CPC ................................................ A61K 2800/874
USPC ........... 514/33, 54.625, 263.34, 460, 263.31, 514/263.32; 424/401; 401/209
See application file for complete search history.

(56) References Cited

U.S. PATENT DOCUMENTS

| | | | |
|---|---|---|---|
| 4,021,125 A | 5/1977 | Berghahn et al. | |
| 4,030,844 A | 6/1977 | Lench et al. | |
| 4,033,700 A | 7/1977 | Spatz | |
| 5,204,105 A * | 4/1993 | Mausner | 424/401 |
| 5,553,957 A | 9/1996 | Dornbusch et al. | |
| 5,676,956 A * | 10/1997 | Duffy et al. | 424/401 |
| D402,550 S | 12/1998 | Poisson | |
| 5,866,158 A * | 2/1999 | Ribier et al. | 424/450 |
| 5,915,592 A * | 6/1999 | Mehus et al. | 222/1 |
| 6,132,126 A | 10/2000 | Sheffler et al. | |
| 6,511,657 B2 | 1/2003 | Avendano et al. | |
| 6,685,062 B1 * | 2/2004 | Ki | 222/321.7 |
| 6,939,071 B1 * | 9/2005 | Breidenbach et al. | 401/209 |
| 2002/0155078 A1 * | 10/2002 | Avendano | A61K 8/03 424/65 |
| 2002/0182158 A1 * | 12/2002 | Christophides-Lordi et al. | 424/64 |
| 2005/0266064 A1 * | 12/2005 | McCarthy | 424/450 |
| 2007/0020220 A1 * | 1/2007 | Osborne | 424/70.14 |

OTHER PUBLICATIONS

Garnier (New Garnier Eye Roll-on [Downloaded Apr. 20, 2011] [Retrieved from internet <URL: http://www.garnier.co.uk/_en/_gb/our_products/products_skincare.aspx?tpcode=OUR_PRODUCTS%5EPRD_SKINCARE%5ECAFFEINE_ SKIN%5ECAFFEINE_SKIN_DISCOVER&prdcode=P19108 >), 1 page.*
Google search results, p. 2, dailymotion.com video link [Downloaded Apr. 20, 2011] [Retrieved from internet <URL: http://www.google.com/search?/sourceid=navclient&ie=UTF-8&oe=UTF-8&q=foll+on+eye+care >], 3 pages.*
Mary Kay Eye Revitalizer (Time Wise ® Targeted-ActionTM Eye Revitalizer, 2007 [Downloaded Apr. 20, 2011] [Retrieved from internet <URL: http://replay.web.archive.org/20071102073433/http://markay.com/skincare/lipeyecare/10011913/10011913/default.aspx >]), 1 page.*
Mary Kay Ask the Experts (FAQ Dark Circles and Puffiness, 2007 [Downloaded Apr. 20, 2011] [Retrieved from internet <URL://http://replay.web.archive.org/20071030193633/http://www.marykay.com/company/researchanddevelopment/faq_puff.aspx?tab=home]), 2 pages.*
TotalBeauty (Mary Kay TimeWise Targeted-Action Eye Revitalizer, Member Reviews, see e.g. Review # 1 (by jopadiet) posted Nov. 17, 2007 [downloaded Apr. 20, 2011] [Retrieved from internet <URL: http://www.totalbeauty.com/reviews/products/504688/mary-kay-timewise-targetedaction-eye-revitalizer >]), 3 pages.*
Maddie (Maddie@BeautyHobby, Dark Circles and Eye Pressure Removal: Garnier Nutritionist Eye Roll-On (Jul. 7, 2008) [Retrieved from internet <URL: http://www.beautyhobby.comlbeauty/skin-care/dark-circles-eye-pressure-removal-garnier-nutritionist-eye-roll-on >], 12 pages).*
SkinBeautiful (Garnier Nutritioniste Skin Renew Anti-Puff Eye Roller (Jul. 26-29, 2008) [Retrieved from internet <URL: http://skinbeautifulblog.wordpress.com/2008/07/16/garnier-nutritioniste-skin-renew-anti-puff-eye-roller/ >], 5 pages).*
SkinRenew (Garnier Skin Care, Skin Renew Anti-Puff Eye Roller, [Retrieved from internet <URL: http://www.garnierusa.com/products/skincare/skin-renew/eye-roller/skin-renew-anti-puff-eye-roller.aspx >] [Downloaded Sep. 26, 2014], 2 pages).*
GCS, Garnier Eye Roll-On Success With Gcs, Global Closure Systems (Jun. 9, 2009) [Retrieved from internet <URL: http://www.gcs.com/markets/personal-care/latest-innovations/articles/garnier-eye-roll-on-success-with-packs-from-gcs/ >], 2 pages.*
Google Search Results, Apr. 20, 2011, 3 pages.*
Garnier (New Garnier Eye Roll-on [Downloaded Apr. 20, 2011] [Retrieved from internet <URL: http://www.garnier.co.uk/en/_gb/our_products/products_skincare.aspx?tpcode=OUR_PRODUCTS%5EPRD_SKINCARE%5ECAFFEINE_ SKIN%5ECAFFEINE_SKIN_DISCOVER&prdcode=P19108 >], 1 page).*
Livestrong, Gwen Bruno, What are the top Anti-Aging Peptides? (Feb. 3, 2014) [Retrieved from internet <URL: http://www.livestrong.com/article/526902-what-are-the-top-anti-aging-peptides/ >], 6 pages, pp. 1- 2.*

(Continued)

Primary Examiner — Ernst V Arnold
Assistant Examiner — Miriam A Levin
(74) Attorney, Agent, or Firm — Oblon, McClelland, Maier & Neustadt, L.L.P.

(57) ABSTRACT

The invention relates to compositions comprising at least one xanthine compound, preferably further comprising at least one agent which acts on capillary circulation and/or at least one natural moisturizing agent, which can be used to treat, or to reduce and/or minimize the appearance of, defects such as dark circles, bags and/or puffiness around eyes.

15 Claims, No Drawings

(56) References Cited

OTHER PUBLICATIONS

Google search results [Downloaded Apr. 20, 2011] [Retrieved from Internet <URL: http://www.google.com/search?/sourceid=navclient&ie=UTF-8&oe=UTF-8&q=foll+on+eye+care>], 3 pages.
New Garnier Eye Roll-on [Downloaded Apr. 20, 2011] [Retrieved from Internet <URL: http://www.garnier.co.uk_en/_gb/our_products/products_skincare.aspx?tpcode=OURPRODUCTS%5EPRD_SKIN CARE%5ECAFFEINE_SKIN%5ECAFFEINE_SKIN_DISCOVER&prdcode=P19108>], 1 page.
Mary Kay TimeWise Targeted-ACtion Eye Revitalizer [Downloaded Apr. 20, 2011] [Retrieved from Internet <URL: http://replay.web.archive.org/20071102073433/http://Www. marykay.com/skincare/lipeyecare/10011913/10011913/default.aspx >1, 1 page.
Mary Kay Ask the Experts [Downloaded Apr. 20, 2011] [Retrieved from Internet <URL: http://replay.web.archive.org/20071030193633/http://vvww.marykay.com/company/researchanddevelopment/faq_puff.aspx?tab= home >], 2 pages.
TotalBeauty, Mary Kay TimeWise Targeted-Action Eye Revitalizer, Member Reviews [Downloaded Apr. 20, 2011] [Retrieved from Internet <URL: http://www.totalbeauty.com/reviews/products/50488/mary-kay-timewise-targetedaction-eye-revitalizer >], 3 pages.
Wikipedia, Guanosine [Downloaded Apr. 21, 2011] [Retrieved from internet <URL: http://en.wikipedia.org/wiki/Guanosine >], 2 pages.

* cited by examiner

COMPOSITIONS AND METHODS FOR MINIMIZING AND/OR REDUCING THE APPEARANCE OF DEFECTS AROUND EYES

CROSS-REFERENCE TO RELATED APPLICATIONS

This application is a continuation of U.S. patent application Ser. No. 12/437,055, filed May 7, 2009, the entire contents of which is hereby incorporated by reference.

FIELD OF THE INVENTION

The present invention relates to compositions such as cosmetic or dermatologic compositions comprising at least one xanthine compound. Preferably, the compositions further comprise at least one agent which acts on capillary circulation and/or at least one natural moisturizing agent. Such compositions can be used, in particular, to treat or to reduce and/or minimize the appearance of defects such as dark circles, bags and/or puffiness around eyes.

DISCUSSION OF THE BACKGROUND

The eye contour (area around the eyes) has a very important aesthetic role since it immediately reflects fatigue, humor and age.

The eye contour, owing to its structure and its high innervation, is an anatomical site that is particularly sensitive to environmental factors (UV rays, pollution, tobacco, etc.) and physiological factors (fatigue, stress, etc.).

In humans, the eyes blink a thousand times per day, and the epidermis which surrounds them is very thin and not very well irrigated—to allow significant mobility, the skin around the eyes is extremely thin (on the order of 0.33 to 0.36 mm, i.e., 3 to 5 times thinner than the rest of the skin of the face). Thus, it is easily dehydrated and vulnerable to external aggressions, meaning that such skin requires particular care.

The skin around the eyes can also reflect one's lifestyle to a certain extent: heat, stress, tobacco, UV rays, and facial expressions can lead to multiple variations of this skin throughout the day which involve vascularization, hydration and turgescence of skin tissues and can help explain the principal changes observed: swelling, dark circles, puffiness, etc.

Moreover, the skin of the eye contour is very reactive due to its richness in inflammatory cells (mast cells), meaning that such skin can be sensitive or intolerant leading, perhaps, to allergic reactions.

Furthermore, the skin of the eye contour can be particularly sensitive to solar radiation. Excessive exposure without protection can lead to redness, sensitivity, or even swelling via microcirculation disorders.

Dark circles and swelling of the eye contour can have a vascular or hereditary origin. Surface vascularization is barely visible in such skin, since the capillaries have a low flow rate, but the vessels of the subcutaneous layers constitute a large vascular reserve which may vary throughout the day. Dark circles generally correspond to a transitory or permanent vascular congestion which results in hyperpigmentation of the skin, and are typically accentuated by at least some of the factors discussed above.

The formation of dark circles often occurs as a result of slowing blood microcirculation, especially at night, which leads to an accumulation of blood pigments in the conjunctive tissue. Furthermore, the lymphatic system, also slowed during the night, leads to swelling of this skin. Such swelling, associated with age-related slackening of the tissues, can help cause the formation of bags.

Defects around eyes such as dark circles and swelling have always been considered to be unattractive, and it has always been a goal to mask them or even eliminate them.

There remains a need for compositions which can reduce and/or minimize the appearance of defects of the contour of the eyes, in particular bags, dark circles and/or puffiness, and for effective methods of reducing and/or minimizing the appearance of such defects in skin around eyes.

SUMMARY OF THE INVENTION

The present invention relates to compositions comprising at least one xanthine compound. Preferably, the compositions further comprise at least one agent which acts on capillary circulation and/or at least one natural moisturizing agent.

The present invention also relates to a roll-on applicator comprising a composition comprising at least one xanthine compound. Preferably, the compositions further comprise at least one agent which acts on capillary circulation and/or at least one natural moisturizing agent.

The present invention further relates to methods for treating defects around eyes such as, for example, dark circles, bags and/or puffiness, comprising topically applying to the skin around eyes a composition comprising at least one xanthine compound. Preferably, the compositions further comprise at least one agent which acts on capillary circulation and/or at least one natural moisturizing agent. Also preferably, application of the composition to the skin around eyes occurs without contacting the composition with human hands and/or fingers prior to application.

The present invention further relates to methods for reducing and/or minimizing the appearance of defects around eyes such as, for example, dark circles, bags and/or puffiness, comprising topically applying to the skin around eyes a composition comprising at least one xanthine compound. Preferably, the compositions further comprise at least one agent which acts on capillary circulation and/or at least one natural moisturizing agent. Also preferably, application of the composition to the skin around eyes occurs without contacting the composition with human hands and/or fingers prior to application.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Contour of the eye" or "around the eye" means an area located around the eye, in particular underneath the eye and the upper eyelid.

"Dark Circle" refers to an area of discoloration in at least a portion of the contour of the eye.

"Puffiness" and "bags" are generally equivalent and mean swelling in at least a portion of the contour of the eye.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The compositions and methods of the present invention can comprise, consist of, or consist essentially of the essential elements and limitations of the invention described herein, as well as any additional or optional ingredients, components, or limitations described herein or otherwise useful.

Compositions Comprising at least One Xanthine Compound

According to the present invention, compositions comprising at least one xanthine compound are provided. Such xanthine compounds can either be the xanthine compound per se or an extract comprising the xanthine compound such as, for example, a natural extract.

Suitable xanthine compounds include, but are not limited to, xanthine compounds per se such as theophylline, caffeine, theobromine, acefylline, xanthinol nicotinate, diniprophylline, diprophylline, etamiphylline and its derivatives, etophylline, proxyphylline, pentophylline, propentophylline, pyridophylline, bamiphylline, and mixtures thereof. Of these, caffeine, theophylline, theobromine, and acefylline are preferred, with caffeine being particularly preferred. An example of a commercially available xanthine compound suitable for use in the invention compositions is caffeine sold by the company BASF (Caffeine Anhydrous Powder).

Suitable xanthine compound containing extracts include, but are not limited to, extracts such as plant extracts such as extracts of tea, of coffee, of guarana, of Paraguay tea, of cola, and mixtures thereof.

In accordance with preferred embodiments, the xanthine compound is preferably present in the composition in an amount of from 0.01% to 10% by weight, preferably from 0.1% to 7% by weight, of the total weight of the composition, including all ranges and subranges therebetween. When an extract containing a xanthine compound is present in the composition, these ranges refer to the amount of xanthine compound per se present, not the amount of extract present.

According to particularly preferred embodiments of the present application, compositions further comprising at least one agent which acts on capillary circulation are provided. Such agents can either be the agent per se or an extract comprising the agent such as, for example, a natural extract.

Suitable agents which act on capillary circulation include, but are not limited to, vasoprotectors and vasodilators, specific examples of which include, for example, flavonoids, extracts of *Ginkgo biloba*, ruscogenins, esculosides, rutin, escin extracted from common horsechestnut, nicotinates, hesperidine methyl chalcone, butcher's-broom, essential oils of lavender or of rosemary, extracts of Ammi Visnaga, and mixtures thereof. According to preferred embodiments, the invention compositions comprise escin. Escin is a mixture of triterpenic pentacyclic acylated saponins obtained from the extraction of the seeds of Horse chestnut (*Aesculus Hippocastanum* L.). An example of commercially available escin is that sold by the company Indena s.p.a. (Escin Free Acid).

In accordance with preferred embodiments, the agent which acts on capillary circulation, if present, is preferably present in the composition in an amount of from 0.01% to 10% by weight, preferably from 0.05% to 5% by weight, of the total weight of the composition, including all ranges and subranges therebetween. When an extract containing an agent which acts on capillary circulation is present in the composition, these ranges refer to the amount of agent per se present, not the amount of extract present.

According to particularly preferred embodiments of the present application, compositions further comprising at least one natural moisturizing agent are provided. A "natural moisturizer" is a naturally occurring biological compound which helps maintain moisturization of the stratum corneum and/or which increases water content of the stratum corneum.

Suitable natural moisturizers include, but are not limited to, lecithins, glycosphingolipids, phospholipids, cholesterol and its derivatives, phytosterols (stigmasterol, β-sitosterol or campesterol), essential fatty acids, hyaluronic acid and its derivatives, ectoin and its derivatives, chitosan, sugars (for example, rhamnose, threalose, glucose), adenosine and its derivatives, ceramides, c-glycosides (for example, modulators of proteoglycans and/or glycoaminoglycans such as those sold under the Pro-xylane® name), and mixtures thereof.

According to particularly preferred embodiments of the present invention, hyaluronic acid or a derivative is present in the composition. Hyaluronic acid belongs to the glycosaminoglycan (GAG) family. GAGs are linear chains composed of a repetition of a base diholoside always containing a hexosamine (glucosamine or galactosamine) and another monosaccharide (glucuronic acid, iduronic acid or galactose). Glucosamine is either N-sulphated or N-acetylated. On the other hand, galactosamine is always N-acetylated. In addition, there may be sulphates O-bonded to the hexosamine, uronic acid and galactose.

Hyaluronic acid or hyaluronan (HA) is the principal GAG of the dermis, the latter containing half the organism's HA. It is a polysaccharide of disaccharides that are themselves composed of D-glucuronic acid and of N-acetylglucosamine, linked to one another via alternating beta-1,4 and beta-1,3 glycosidic bonds.

According to preferred embodiments, the composition according to the present invention contains hyaluronic acid and/or one of its salts. Suitable hyaluronic acid salts include, but are not limited to, potassium hyaluronate and sodium hyaluronate, with sodium hyaluronate being particularly preferred. For example, sodium hyaluronate with a molecular weight of 1,100,000 daltons, sold by the company SOLIANCE under the name CRISTALHYAL®, may be used.

In accordance with preferred embodiments, the natural moisturizing agent, if present, is preferably present in the composition in an amount of from 0.01% to 5% by weight, preferably from 0.01% to 3% by weight, preferably from 0.01 to 1% by weight, of the total weight of the composition, including all ranges and subranges therebetween. When a product containing a natural moisturizing agent is present in the composition, these ranges refer to the amount of agent per se present, not the amount of product present.

In accordance with the present invention, the composition comprising at least one xanthine compound, preferably further comprising at least one agent which acts on capillary circulation and/or at least one natural moisturizing agent, comprises active agent(s) present, alone or in any combination thereof, in an amount sufficient to treat defects of the eye contour, particularly bags, puffiness and/or dark circles, or to reduce and/or minimize the appearance of defects of the eye contour, particularly bags, puffiness and/or dark circles. Such effects may be measured by simple visual observation or by comparative image analysis.

The composition of the invention can further optionally comprise any additive usually used in the field under consideration. For example, vitamins such as vitamin A, vitamin B, vitamin C, vitamin D, etc., and derivatives thereof such as, for example, retinol, retinyl palmitate, panthenol and in particular D-panthenol, ascorbyl palmitate, etc., oils, water, pigments, solvents such as polyols and in particular butylene glycol and/or glycerine, film forming agents, dispersants, antioxidants, sunscreens, preserving agents, fragrances, fillers, neutralizing agents, surfactants, emulsifiers, hydrophilic or lipophilic gelling agents, hydrophilic or lipophilic additives, screening agents, ph adjusters, colorants, sequestrants, chelating agents, odor absorbers and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002). Other ingredients such as Guanosine and Hydroxyproline, may also be added.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the contour of the eye of human beings. The composition may be in any galenic form normally employed in the cosmetic and dermatological fields which is suitable for topical administration onto skin. Aqueous compositions are preferred, with aqueous compositions in the form of a gel being particularly preferred. If the composition is in the form of a gel, the composition preferably comprises at least one gelling agent which may be any gelling agent suitable for use in the cosmetic area. For example, suitable gelling agents include, but are not limited to, carboxyvinyl polymers (carbomer), acrylic copolymers such as acrylate/alkyl acrylate copolymers, polyacrylamides optionally in the form of copolymers in an inverse emulsion, such as the products sold, respectively, by CLARIANT under the trade name HOSTACERIN AMPS and by SEPPIC under the trade name SEPIGEL 305, polysaccharides, such as xanthan gum. In such gel compositions, the water content is preferably higher than 50% of the total weight of the composition.

Methods of Addressing Defects Around the Eyes Using the Composition of the Present Invention According to preferred embodiments of the present invention, methods of treating defect(s) of the contour of the eye comprising applying a composition of the present invention to the contour of the eye in an amount sufficient to treat the defect(s) are provided.

According to other preferred embodiments, methods of reducing and/or minimizing the appearance of defect(s) of the contour of the eye comprising applying a composition of the present invention to the contour of the eye in an amount sufficient to reduce and/or minimize the appearance of the defect(s) are provided.

In accordance with preferred embodiments of the preceding methods, a composition of the present invention comprising at least one xanthine compound, preferably further comprising at least one agent which acts on capillary circulation and/or at least one natural moisturizing agent, are applied topically to the contour of the eye of a person in need of the desired treatment, reduction and/or minimization in an amount sufficient to achieve the desired result. The compositions may be applied to the desired area as needed, preferably once or twice daily.

Preferably, application begins at the inner corner of the eye (proximate to the nose), and continues along the contour toward the outer corner of the eye. However, the reverse direction of application can also occur.

According to particularly preferred embodiments, application of the composition to the skin around eyes occurs without contacting the composition with human hands and/or fingers prior to application. That is, application occurs via an applicator which enables the user to avoid contacting the composition prior to application. Such application, without contact with human skin prior to application, can improve efficacy of the composition. Although not wishing to be bound by any particular theory, it is believed that such pre-application contact raises the temperature of the composition prior to application, which can have the effect of negatively affecting the composition's efficacy.

Suitable application methods (without contacting the user's hands or fingers) include but are not limited to application using a roll-on dispenser or applicator (for example, the type of dispenser or applicator used to apply roll-on deodorants) and application using an applicator pad or wipe.

According to particularly preferred embodiments of the present invention, a roll-on dispenser or applicator is used to apply the composition of the present invention to the contour of the eye. In accordance with such preferred embodiments, the roll-on dispenser or applicator comprises a reservoir having a base and, opposite the base, an opening. The reservoir can be made of various materials such as, for example, glass or a plastic like polypropylene, polyethylene terephthalate (PET), acrylobutadiene styrene (ABS), or polyethylene, and can be of any shape. The reservoir contains the composition of the present invention.

Mounted in the opening is a rotatable ball which, for example, can be assembled directly in the reservoir or through a special insert (ball housing) depending on the size and design of the reservoir. Typically, the rotatable ball is hollow. The rotatable ball can be of any suitable material such as, for example, glass, plastic (such as those mentioned above in connection with the reservoir) or metal. Metals such as, for example, stainless steel, aluminum, and silver may be used, with stainless steel being preferred. The diameter of the ball will, of course, vary depending on the size of the opening in the reservoir. Preferably, the rotatable ball does not substantially change the temperature of the composition of the present application during application. During application, the composition of the present invention is applied to the skin of the contour of the eye through the rotating or rolling action of the rotatable ball.

Examples of suitable roll-on dispensers include those described in U.S. Des. Pat. No. 402,550, and U.S. Pat. Nos. 6,511,657, 6,132,126, 4,030,844, 4,021,125, 4,033,700, and 5,553,957, all of which are incorporated by reference herein including their drawings to the extent they describe roll-on dispensers.

The present invention also relates to a roll-on applicator as described above comprising a composition comprising at least one xanthine compound. Preferably, the compositions further comprise at least one agent which acts on capillary circulation and/or at least one natural moisturizing agent.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1

Composition

| Ingredient | Amount |
| --- | --- |
| BUTYLENE GLYCOL | 5 |
| XANTHAN GUM | 0.4 |
| CAPRYLYL GLYCOL | 0.3 |
| GUANOSINE | 0.01 |
| DISODIUM EDTA | 0.2 |
| BIOSACCHARIDE GUM-1 | 5 |
| POLYACRYLAMIDE (and) C13-14 ISOPARAFFIN (and) LAURETH-7 | 0.4 |
| HYDROXYPROLINE | 0.3 |
| GLYCERIN | 3 |
| CAFFEINE | 0.5 |
| ESCIN | 0.05 |
| WATER | 83.87 |
| PANTHENOL | 0.5 |
| SODIUM HYALURONATE | 0.02 |
| PRESERVATIVE AGENTS | 0.45 |
| Total: | 100 |

Example 2

Application of the Composition of Example 1 to the Contour of the Eye—Moisturizing Effect The composition of example 1 was placed into a roll-on dispenser. 24 subjects applied the composition of example 1 to the contour of their eyes using the dispenser a single time. The skin of the subjects thus-treated 4 hours after application as well as 8 hours after application was compared to the skin prior to treatment. The subjects' skin was evaluated using a corneometer which estimated the water content in stratum corneum of the skin from electric capacitance—the higher the water content, the higher the conductance or electric capacitance of skin surface. Via this method, the water content of the stratum corneum was quantitatively determined. The results are set forth below.

| | Improvement vs T0 |
| --- | --- |
| T4 hours | +21% |
| T8 hours | +15% |

The composition of example 1 when applied to skin using a roll-on dispenser had a significant moisturizing effect 4 hours after application as well as 8 hours after application as compared to non-treated skin.

Example 3

Application of the Composition of Example 1 to the Contour of the Eye—Effect on Bags and Dark Circles The composition of example 1 was placed into a roll-on dispenser. 151 subjects applied the composition of example 1 to the contour of their eyes using the dispenser, twice a day, for four weeks. 50 of these subjects were subjected to clinical grading; 101 subjects were subject to self-assessment. All of the subjects had bags and/or dark circles in the contour of the eyes. All skin types were represented in the group of 151. The results are set forth below.

Clinical Grading—Efficacy on Dark Circles and Bags

Dermatologists evaluated the bags and dark circles of 50 subjects and determined:

| | Improvement after 4 weeks |
| --- | --- |
| Bags | −11% |
| Dark circles | −12% |

The composition of example 1 when applied to skin using a roll-on dispenser had a significant effect on both bags and dark circles after 4 weeks of use.

Self Assessment—Perceived Efficacy 101 subjects were provided questionnaires concerning the efficacy of the composition of example 1. Their answers are set forth below.

| | T Immediate | T4 weeks |
| --- | --- | --- |
| Skin looks more hydrated | 86% | 93% |
| Skin feels more comfortable | 88% | 89% |
| Skin looks more uniform | 63% | 85% |
| Upper eyelids look less puffy | — | 77% |
| The product brings freshness upon application | 94% | |
| The product does not leave skin sticky | — | 92% |
| The product does not leave skin greasy | — | 100% |
| The product does not leave skin shiny | — | 95% |

Example 4

Comparison of Application Methods

The composition of example 1 was placed into a roll-on dispenser for application. 23 subjects, women ranging from 21 to 50 years old, applied the composition of example 1 to the contour of their eyes a single time. Application to the contour of the eye on one side of the face occurred using a finger. Application to the contour of the eye on the other side of the face occurred using the roll-on dispenser. The sides were randomized among the women. The skin of the subjects thus-treated was evaluated by IR camera. The results were as follows.

The composition applied with the fingers yielded a fresh effect in 1 min., 41 sec. (corresponding to a decrease of initial temperature (−2.6° C.)).

In contrast, the composition applied using a roll-on dispenser yielded a fresh effect in 59 seconds (corresponding to a decrease of initial temperature (−2.1° C.)). This time differential in achieving the temperature decrease (fresh effect) was statistically significant Application using a roll-on dispenser permitted obtaining the fresh effect more quickly.

What is claimed is:

1. A roll-on applicator comprising a reservoir and a rotatable application surface capable of being in fluid communication with the reservoir, wherein in said applicator a composition comprising at least one xanthine compound, at least one agent which acts on capillary circulation, and at least one natural moisturizing agent is present within said reservoir,
wherein
the at least one natural moisturizing agent is sodium hyaluronate,
the at least one xanthine compound is caffeine, and
the at least one agent which acts on capillary circulation is escin.

2. A roll-on applicator according to claim 1, wherein the rotatable application surface is an outer surface of a sphere made from metal, glass, plastic or ceramic.

3. The roll-on applicator of claim 1, wherein the composition further comprises a vitamin compound.

4. The roll-on applicator of claim 3, wherein the vitamin compound is panthenol.

5. The roll-on applicator of claim 1, wherein the composition further comprises guanosine and/or hydroxyproline.

6. The roll-on applicator of claim 1, wherein the rotatable application surface is metal.

7. The roll-on applicator of claim 1, wherein the xanthine compound is present in the composition in an amount of from 0.1% to 7% by weight, of the total weight of the composition.

8. The roll-on applicator of claim 1, wherein the agent which acts on capillary circulation is present in the composition in an amount of from 0.05% to 5% by weight, of the total weight of the composition.

9. The roll-on applicator of claim 1, wherein the natural moisturizing agent is present in the composition in an amount of from 0.01 to 1% by weight, of the total weight of the composition.

10. The roll-on applicator of claim 1, wherein the reservoir is made of glass or plastic selected from the group consisting of polypropylene, polyethylene terephthalate, acrylobutadiene styrene and polyethylene.

11. The roll-on applicator of claim 1, wherein the composition further comprises water.

12. The roll-on applicator of claim 11, wherein the composition comprises at least one additive and at least one gelling agent.

13. A method of reducing or minimizing dark circles, bags or puffiness on the contours of eyes of a person in need thereof comprising applying a composition comprising at least one xanthine compound, at least one agent which acts on capillary circulation, and at least one natural moisturizing agent to the contours of eyes using a roll-on applicator of claim 1 in an amount sufficient to minimize or reduce the bags, dark circles or puffiness, wherein
the natural moisturizing agent is sodium hyaluronate,
the at least one xanthine compound is caffeine, and
the at least one agent which acts on capillary circulation is escin.

14. The method of claim 13, wherein the composition further comprises a vitamin compound.

15. The method of claim 14, wherein the vitamin compound is panthenol.

* * * * *